US010553308B2

(12) United States Patent
Baldwin

(10) Patent No.: US 10,553,308 B2
(45) Date of Patent: Feb. 4, 2020

(54) IDENTIFYING MEDICALLY RELEVANT PHRASES FROM A PATIENT'S ELECTRONIC MEDICAL RECORDS

(71) Applicant: International Business Machines Corporation, Armonk, NY (US)

(72) Inventor: Tyler Baldwin, Union City, CA (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 15/856,338

(22) Filed: Dec. 28, 2017

(65) Prior Publication Data

US 2019/0206522 A1    Jul. 4, 2019

(51) Int. Cl.
| | |
|---|---|
| *G06F 17/24* | (2006.01) |
| *G16H 10/60* | (2018.01) |
| *G06F 17/27* | (2006.01) |
| *G06F 16/338* | (2019.01) |
| *G06F 16/38* | (2019.01) |
| *G06F 16/332* | (2019.01) |
| *G06F 16/33* | (2019.01) |
| *G06N 20/00* | (2019.01) |

(52) U.S. Cl.
CPC ........... *G16H 10/60* (2018.01); *G06F 16/338* (2019.01); *G06F 16/3329* (2019.01); *G06F 16/3344* (2019.01); *G06F 16/382* (2019.01); *G06F 17/241* (2013.01); *G06F 17/2775* (2013.01); *G06N 20/00* (2019.01)

(58) Field of Classification Search
CPC ...................................................... G06Q 10/10
See application file for complete search history.

(56) References Cited

U.S. PATENT DOCUMENTS

| | | | |
|---|---|---|---|
| 6,263,335 B1 * | 7/2001 | Paik | ................. G06F 17/30707 |
| 7,533,089 B2 | 5/2009 | Pan et al. | |
| 8,275,803 B2 | 9/2012 | Brown et al. | |
| 9,367,608 B1 | 6/2016 | Zhang | |
| 2007/0174041 A1 | 7/2007 | Yeske | |
| 2008/0300856 A1 | 12/2008 | Kirk et al. | |

(Continued)

OTHER PUBLICATIONS

List of IBM Patents or Patent Applications Treated as Related, May 10, 2018, 2 pages.

(Continued)

*Primary Examiner* — Sanchita Roy
(74) *Attorney, Agent, or Firm* — Francis Lammes; Stephen J. Walder, Jr.; William J. Stock

(57) ABSTRACT

Mechanisms are provided to implement a natural language request processing engine (NLRPE). The NRLPE performs natural language processing on a portion of unstructured text in an electronic data structure to generate textual characteristics of the portion of unstructured text. The NRLPE annotates at least one phrase in the portion of unstructured text at least by linking the at least one phrase to one or more concepts specified in at least one ontological data structure based on the textual characteristics of the portion of unstructured text. The NRLPE generates a model of the portion of unstructured text based on the one or more concepts linked to the at least one phrase. The NRLPE processes a request for information specifying a concept of interest based on the model of the portion of unstructured text by retrieving the at least one phrase as a response.

20 Claims, 8 Drawing Sheets

(56) References Cited

U.S. PATENT DOCUMENTS

| | | | |
|---|---|---|---|
| 2009/0287678 A1 | 11/2009 | Brown et al. | |
| 2011/0066587 A1 | 3/2011 | Ferrucci et al. | |
| 2011/0087670 A1 | 4/2011 | Jorstad et al. | |
| 2011/0125734 A1 | 5/2011 | Duboue et al. | |
| 2012/0215559 A1* | 8/2012 | Flanagan | G06Q 10/10 705/3 |
| 2013/0007055 A1* | 1/2013 | Brown | G06F 17/30654 707/769 |
| 2013/0018652 A1 | 1/2013 | Ferrucci et al. | |
| 2013/0066886 A1 | 3/2013 | Bagchi et al. | |
| 2013/0138457 A1 | 5/2013 | Ragusa | |
| 2013/0268260 A1 | 10/2013 | Lundberg et al. | |
| 2014/0365210 A1* | 12/2014 | Riskin | G06F 17/2765 704/9 |
| 2015/0112664 A1 | 4/2015 | Srinivasan | |
| 2016/0019299 A1* | 1/2016 | Boloor | G06F 17/30867 705/3 |
| 2016/0140858 A1 | 5/2016 | Adderly et al. | |
| 2016/0147875 A1 | 5/2016 | Adderly et al. | |
| 2016/0224542 A1 | 8/2016 | Bulgakov et al. | |
| 2018/0060305 A1 | 3/2018 | Deleris et al. | |
| 2018/0082183 A1* | 3/2018 | Hertz | G06F 17/30675 |

OTHER PUBLICATIONS

Aronson, Alan R., "Effective Mapping of Biomedical Text to the UMLS Metathesaurus: The MetaMap Program", American Medical Informatics Association, Proceedings of the AMIA Symposium, (month unknown) 2001, pp. 17-21.

Bill, Robert et al., "Automated Extraction of Family History Information from Clinical Notes", American Medical Informatics Association, AMIA Annual Symposium Proceedings, vol. 2014, Nov. 14, 2014, pp. 1709-1717.

Cheng, Ching K. et al., "Ontology-based Semantic Classification of Unstructed Documents", Springer-Verlag Berlin Heidelberg, AMR 2003, LNCS, vol. 3094, Jul. 2004, pp. 120-131.

Conway, Mike et al., "Using Chief Complaints for Syndromic Surveillance: A Review of Chief Complaint Based Classifiers in North America", Elsevier, Journal of Biomedical Informatics, vol. 46, No. 4, Aug. 2013, pp. 734-743.

High, Rob, "The Era of Cognitive Systems: An Inside Look at IBM Watson and How it Works", IBM Corporation, *Redbooks*, Dec. 12, 2012, 16 pages.

Jackson, Richard G. et al., "TextHunter—A User Friendly Tool for Extracting Generic Concepts from Free Text in Clinical Research", American Medical Informatics Association, AMIA Annual Symposium Proceedings, vol. 2014, Nov. 14, 2014, pp. 729-738.

Liu, Kaihong et al., "Natural Language Processing Methods and Systems for Biomedical Ontology Learning", Elsevier, Journal of Biomedical Informatics, vol. 44, No. 1, Feb. 2011, pp. 163-179.

McCord, M.C. et al., "Deep parsing in Watson", IBM J. Res. & Dev. vol. 56 No. 3/4 Paper 3, May/Jul. 2012, pp. 3:1-3:15.

Savova, Guergana K. et al., "Mayo clinical Text Analysis and Knowledge Extraction System (cTAKES): architecture, component evaluation and applications", American Medical Informatics Association, Journal of the American Medical Informatics Association, vol. 17, No. 5, Sep. 1, 2010; pp. 507-513.

Sun, Jimeng et al., "Combining Knowledge and Data Driven Insights for Identifying Risk Factors using Electronic Health Records", American Medical Informatics Association, AMIA Annual Symposium Proceedings, vol. 2012, Nov. 3, 2012, pp. 901-910.

Yuan, Michael J., "Watson and Healthcare, How natural language processing and semantic search could revolutionize clinical decision support", IBM Corporation, developerWorks, http://www.ibm.com/developerworks/industry/library/ind-watson/, Apr. 12, 2011, 14 pages.

Zheng, Jiaping et al., "Automatically Detecting Acute Myocardial Infarction Events from EHR Text: A Preliminary Study", American Medical Informatics Association, AMIA Annual Symposium Proceedings, vol. 2014, Nov. 14, 2014, pp. 1286-1293.

* cited by examiner previous history of recent hypertension or HT

Phrase Start → Internal Phrase → Internal Phrase → Internal Phrase → Internal Phrase

*FIG. 4A* previous history of recent hypertension or HT

Phrase Start → Internal Phrase → Internal Phrase → Internal Phrase → Internal Phrase

*FIG. 4B*

60 year old man presents to the office with a history of hemoptysis and negative history for previous PE. Heart rate of 60 b.p.m. No previous history of recent surgery or immobilization. No symptoms found for DVT and no past history for malignancy.

Detected Types:
Social History
Past Medical History
Past Surgical History
History of Present Illness
Physical Exam

FIG. 5

This patient returns to Cardiology Clinic and does not feel well today. He thinks that he had a tia yesterday in which he had sudden right arm weakness. His EKG today shows atrial fibrillation with a controlled ventricular response, and T wave inversions consistent with ischemia.

*FIG. 6*

015
IDENTIFYING MEDICALLY RELEVANT PHRASES FROM A PATIENT'S ELECTRONIC MEDICAL RECORDS

BACKGROUND

The present application relates generally to an improved data processing apparatus and method and more specifically to mechanisms for identifying medically relevant phrases from a patient's electronic medical records.

Information retrieval and information extraction are significant issues in the medical and health care domains where the accuracy of the retrieved information and obtaining it in a time critical situation are extremely important. Information retrieval (IR) is the activity of obtaining information resources relevant to an information need from a collection of information resources. Searches can be based on full-text or other content-based indexing. Information retrieval is the science of searching for information in a document, searching for documents themselves, and also searching for metadata that describe data, and for databases of texts, images or sounds. Information extraction (IE) is the task of automatically extracting structured information from unstructured and/or semi-structured machine-readable documents. In most of the cases this activity concerns processing human language texts by means of natural language processing (NLP).

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system comprising a processor and a memory, the memory comprising instructions that are executed by the processor to specifically configure the processor to implement a natural language request processing engine. The method comprises performing, by the natural language request processing engine, natural language processing on a portion of unstructured text in an electronic data structure to generate textual characteristics of the portion of unstructured text. The method also comprises annotating, by the natural language request processing engine, at least one phrase in the portion of unstructured text at least by linking the at least one phrase to one or more concepts specified in at least one ontological data structure based on the textual characteristics of the portion of unstructured text. In addition, the method comprises generating, by the natural language request processing engine, a model of the portion of unstructured text based on the one or more concepts linked to the at least one phrase. Further, the method comprises processing, by the natural language request processing engine, a request for information specifying a concept of interest based on the model of the portion of unstructured text, wherein the processing of the request for information comprises retrieving the at least one phrase as a response to the request in response to the at least one phrase having an associated concept in the one or more concepts that matches the concept of interest specified in the request.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 4A depicts one example of labeling instances within a phrase with start of phrase and internal phrase labels in accordance with an illustrative embodiment;

FIG. 4B depicts one example of converting an internal phrase label to an end of phrase label in accordance with an illustrative embodiment;

FIG. 5 below shows one example of detected phrases and their corresponding categories in accordance with an illustrative embodiment;

FIG. 6 below shows one example of detected phrases which have been further merged in accordance with an illustrative embodiment;

DETAILED DESCRIPTION

Figure 1:
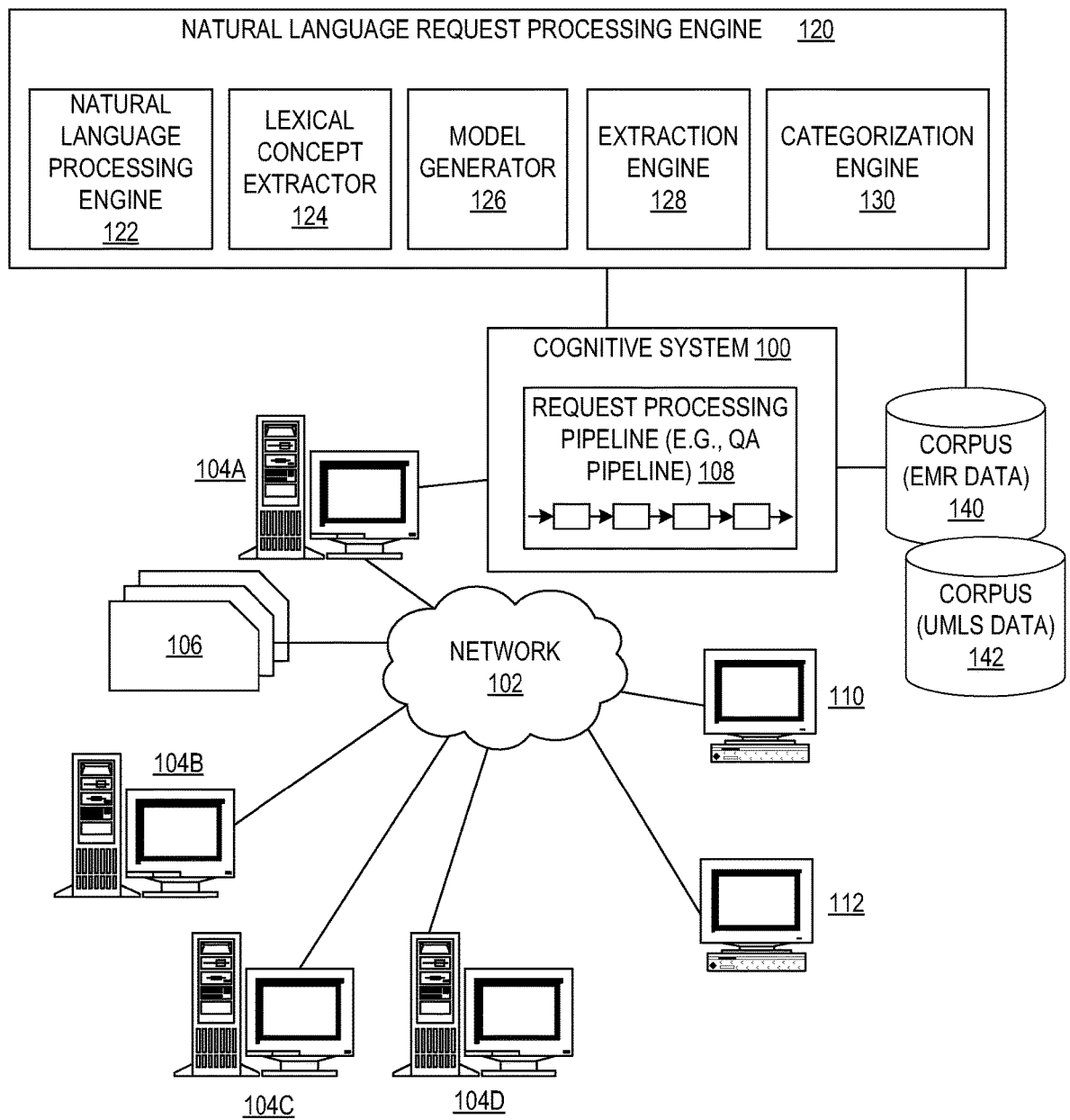
FIG. 1 depicts a schematic diagram of one illustrative embodiment of a cognitive healthcare system in a computer network.

The strengths of current cognitive systems, such as current medical diagnosis, patient health management, patient treatment recommendation systems, law enforcement investigation systems, and other decision support systems, are that they can provide insights that improve the decision making performed by human beings. For example, in the medical context, such cognitive systems may improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of applications as well as more representative of the way in which human beings make decisions, such as diagnosing and treating patients. In particular, one drawback of current systems is that much of the medically relevant information in a patient's electronic medical records (EMR) is recorded only as medical notes such as discharge reports, consult documents, procedure notes, or the like, all of which is not currently extracted by existing extraction mechanisms because this medically relevant information may be at a different level of granularity than the original text, may be missing contextual information, and may provide a poor representation of medical expectations.

In order to have a holistic overview of a patient's condition, medical professionals need to be able to access this medically relevant information in a timely and coherent manner. The illustrative embodiments provide mechanisms for phrase-based extraction that is anchored to concepts, allowing for the medically relevant portions of text within the patient's EMR to be extracted. Utilizing Natural Language Processing (NLP), unstructured (natural language) text within the patient's EMR is analyzed and, based on the results of the NLP, concepts are extracted and those concepts are linked to an ontology. The concepts provide anchor points for phrases in the unstructured text. The text corresponding to a related concept is then concatenated to generate the phrases that are anchored to the concepts and thereby generate medically relevant phrases that are then provided to the medical professional requesting information regarding the corresponding concept (anchor point).

Additionally, the illustrative embodiments provide mechanisms for categorizing the medically relevant phrases into medical categories. Labels are associated with the medical categories and these labels are used to analyze other medically relevant phrases in the natural language content of the patient's EMR to determine which medical category these other medically relevant phrases are associated with. Determinations are then made with regard to merging medically relevant phrases in the same natural language content, based on medically relevant phrases being associated with a same medical category. A Conditional Random Field approach may be used to determine whether to merge medically relevant phrases. That is, Conditional Random Field (CRF) models may be used to model what is a medically relevant phrase. The CRF models model the sequential aspect of a medically relevant phrase and thus, may be used to perform pattern recognition with a portion of unstructured text. Thus, the mechanisms describe medically relevant phrases as CRF models and find these CRF models in segmented text generated by the NLP of the patient's EMR where the segments are specified by the anchor points associated with the concepts.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for phrase-based extraction that is anchored to concepts, allowing for the medically relevant portions of text within the patient's EMR to be extracted as well as categorizing the medically relevant phrases into medical categories.

Figure 2:
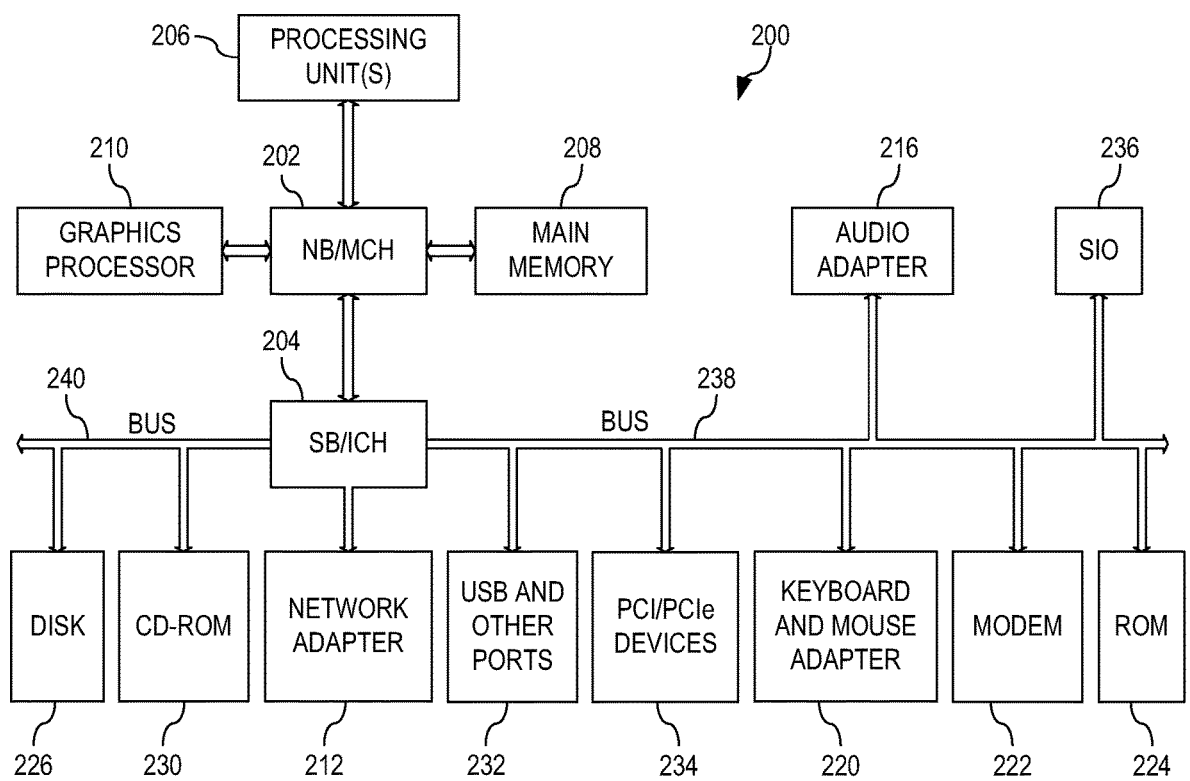
FIG. 2 is a block diagram of an example data processing system in which aspects of the illustrative embodiments are implemented.
Figure 3:
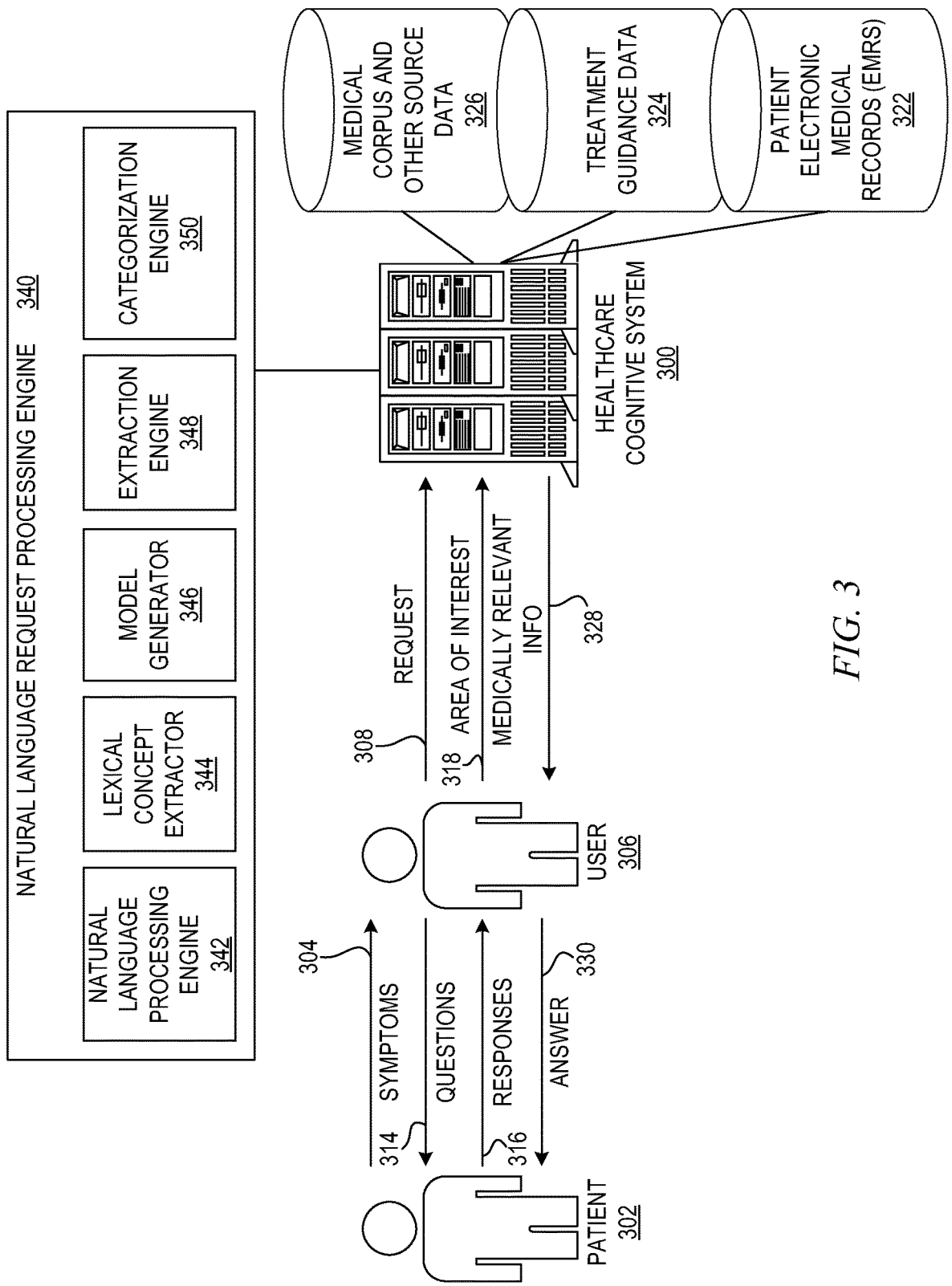
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for medically relevant phrase identification and categorization.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with Which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to automatic phrase-based extraction anchored to concepts, allowing for the medically relevant portions of text within the patient's EMR to be extracted and automatic categorizing of the medically relevant phrases into medical categories.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document, from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e., candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables question processing and answer generation (QA) functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108 which comprises a plurality of stages for processing an input question/request based on information obtained from the corpus or corpora of data 106. The pipeline 108 generates answers/responses for the input question or request based on the processing of the input question/request and the corpus or corpora of data 106. The pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process is be repeated for each of the candidate answers to generate ranked listing of candidate answers which may then be presented to the user that submitted the input question, e.g., a user of client computing device 110, or from which a final answer is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a natural language request processing engine that analyzes unstructured (natural language) text within the patient's electronic medical records (EMR) and, based on the results of the NLP analysis, extracts concepts that are linked to an ontology. The concepts provide anchor points for phrases in the unstructured text. The natural language request processing engine concatenates text portions corresponding to a similar concept to generate phrases that are anchored to the concepts and thereby generate medically relevant phrases. The natural language request processing engine then provides the medically relevant phrased to the medical professional requesting information regarding the corresponding concept (anchor point). Additionally, the natural language request processing engine categorizes the medically relevant phrases into medical categories.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a natural language request processing engine 120. Natural language request processing engine 120 comprises natural language processing engine 122, lexical concept extractor 124, model generator 126, and extraction engine 128.

In the initial stage of processing, natural language request processing engine 120 receives an expectation from a medical professional indicating an area of interest that the medical professional would like to identify from the unstructured text of the patient's electronic medical records (EMR) 140, i.e. medical notes made by other medical professionals. For example, if the medical professional is interested in seeing if the patient has a history of 'Hypertension,' the medical professional will enter "hypertension" into natural language request processing engine 120. Accordingly, natural language processing engine 122 analyzes the structure of unstructured text in a medical document using known natural language processing techniques, including part-of-speech tagging, dependency parsing, negation detection, or the like, Lexical concept extractor 124 then identifies medical concepts in the unstructured text and matches not only the area of interest entered by the medical professional but also related medical concepts identified using existing concept ontologies, such as an Unified Medical Language System (MILS) ontology 142, which is a knowledge base created by the National Library of Medicine. There are multiple ways in which medical professionals may mention hypertension when describing a patient. Thus, using related medical concepts, lexical concept extractor 124 may identify hypertension as well as surface variations such as 'HT' or 'HTN', as well as semantic variations such as 'High Blood Pressure' or 'Hypertensive disease NOS' or 'BP+' etc.

Once the structure and content of the unstructured text has been analyzed, model generator 126 constructs a Conditional Random Field (CRT) model as an undirected graphical model. In the undirected graphical model, model generator 126 constructs a representation such that each concept in the unstructured text is represented by a node. Model generator 126 then links these nodes together in a linear fashion such that a node is linked to both the concept found directly before the concept in the unstructured text and the concept found directly after the concept in the unstructured text.

Model generator 126 also constructs an additional link to a latent variable node, representing the label to be inferred. In order to infer the label, model generator 126 utilizes annotated data of sentences with medical phrases. Model generator 126 labels concepts in the ground truth text that begin a phrase of interest as a start of phrase label, while also labeling instances within the phrase with an internal phrase label, as illustrated in FIG. 4A in accordance with an illustrative embodiment. As shown in the FIG. 4A, the intended phrase of interest "previous history of recent surgery or immobilization" contains several medical concepts from the base ontology, i.e. "previous", "history", "recent", "surgery", and "immobilization". Model generator 126 labels the initial concept in the phrase, "previous", as the start of the phrase, while labeling all other concepts as internal to the phrase. Phrase endings are inferred by examining the label associated with the next concept in the sentence. That is, if model generator 126 identities a next concept as a phrase start label, then the previous internal phrases is relabeled as an end of the phrase, as illustrated in FIG. 4B in accordance with an illustrative embodiment.

To generalize the associations present in the annotated data, model generator 126 utilizes an array of discriminative features. These features are extracted from the concept information available within the linked ontology, the natural language processing analysis of the unstructured text, the words in the unstructured text found near the concept of interest, or the like. The linear connectedness of the graphical model ensures that each concept within the unstructured text is dependent on the concepts immediately preceding the concept and the concepts immediately following the concept, enabling model generator 126 to discover which concepts are appropriately grouped within the same phrase. In this manner, model generator 126 discovers text phrases with an underlying conceptual anchoring, enabling model generator 126 to capture the necessary context while still benefiting from the ontology information associated with each concept.

Having identified one or more medically relevant phrases in the unstructured text and associating them with medical concepts as anchor points, extraction engine 128 extracts each one or more medically relevant phrases and returns the one or more medically relevant phrases to the medical professional who requested the information about a particular medical concept or related medical concept. Thus, if a medical professional wants to know about a patient's particular condition, the related medical concepts may be determined and then used to identify the medically relevant phrases within the patient's EMR linked to the requested medical concept, including those phrases in the natural language medical notes processed by natural language request processing engine 120, such that these medically relevant phrases may be returned to the medical professional as a response to their inquiry. Thus, natural language request processing engine 120 automatically finds medically relevant phrases utilizing a process that is not dependent on rules but, rather, is linked to anchor medical concepts.

In addition to the above, natural language request processing engine 120 also comprises categorization engine 130 that categorizing medically relevant phrases into medical categories or buckets, which have associated labels. Categorization engine 130 then utilizes these labels to analyze other phrases in the natural language content to determine whether these other phrases are associated with the requested medical concept. Determinations as to whether to merge phrases in the same natural language content, based on phrases being associated with a same category, may then be made. The CRF model approach may be used to determine whether to merge phrases.

For example, given an identified first medically relevant phrase from the unstructured text, categorization engine 130 categorizes the medically relevant phrase into a predefined category or bucket, which has label associated with the category of the medically relevant phrase. Categorization engine 130 utilizes the category or bucket labels as a basis for identifying other phrases in the unstructured text that are associated with similar concepts and that may be categorized into the same category. If another phrase is identified in the unstructured text that may be categorized in the same category based on a correlation of the labels of the category with the medically relevant phrase or anchor point associated with the medically relevant phrase, categorization engine 130 determines Whether the other medically relevant phrases should be merged with the identified and categorized first medically relevant phrase to generate a merged phrase associated with the category and clinical concept anchor point or the original medically relevant phrase. This determination of whether to merge phrases may be performed based on a set of conditional random fields (CRF), for example.

FIG. 5 below shows one example of detected phrases and their corresponding categories in accordance with an illustrative embodiment. Through the mechanisms of the illustrative embodiments, natural language processing engine 122, lexical concept extractor 124, and model generator 126 detect the medically relevant phrase "history of hemoptysis" associated with a concept anchor point. Categorization engine 130 then categorizes the medically relevant phrase into a category of clinical concepts, e.g., "past medical history", which has associated labels, e.g. terms that may be used to match with other phrases, e.g., the term "history". The classification may be from annotations produced by clinicians, and may be based on features from NLP, concept info, document structure, words, sequence, or the like. The classification of adjacent phrases by categorization engine 130 into a same category gives evidence for further phrase merging. Thus, for example, the phrases "history for previous PE", "immobilization", and "past history for malignancy" are other phrases that may be identified as classifiable into the same classification as the first phrase and potential candidates for merging.

Once phrases have been identified and categorized, and additional CRF model is constructed to perform the merging of phrases. While not directly anchored to medical concepts as performed by model generator 126 to produce larger phrases, the observed nodes of the CRF model utilized in merging are the phrases produced as output of the previous CFR models constructed by model generator 126. In this way the CRF model generated by categorization engine 130 inherits the properties of the underlying CRF model, including its concept anchors.

FIG. 6 below shows one example of detected phrases which have been further merged in accordance with an illustrative embodiment. FIG. 6 contains one example of a merged medically relevant phrase, "EKG today shows atrial fibrillation with a controlled ventricular response, and T wave inversions consistent with ischemia". Before merging, the medically relevant phrase comprised three separate phrases ("EKG", "atrial fibrillation with a controlled ventricular response", "T wave inversions consistent with ischemic"), as identified by model generator 126 and further classified by categorization engine 130 the initial stage of processing described previously. To identify the need for merging, categorization engine 130 constructs a CRF model anchored to these previously identified medically relevant phrases. The structure of this CRF model is linear, such that each phrase is represented as a node with a single edge connecting the node to the preceding medically relevant phrases and following medically relevant phrases in unstructured text. Each node also has an edge connecting it with a latent variable, representing the label of interest to be inferred. Much like the previous CRF model which categorization engine 130 works on top of, the labels of interest are represented by phrase start, phrase internal, and phrase end labels associated with each of the clinical categories.

Once the CRF model has been constructed, categorization engine 130 utilizes annotated data to establish a ground truth for model construction. To ensure the model is able to successfully learn how to combine phrases, categorization engine 130 constructs a discriminative feature space from features extracted from several source, such as features derived from the NLP-based analysis of unstructured text and document structure, concept ontology information, adjacent non-concept words, or the like. In addition to this, the output of the previous CRF model provides features for phrase labels. The label associated with the phrase as well as the classifiers probability distribution over all possible labels are included in the feature set.

Having identified and merged concepts that are categorized into a category that is relevant to the area of interest identified by the medical professional, extraction engine 128 extracts each one or more medically relevant phrases and returns the one or more medically relevant phrases to the medical professional who requested the information about a particular medical concept or related medical concept. Thus, if a medical professional wants to know about a patient's particular condition, the related medical concepts may be determined and then used to identify the medically relevant phrases within the patient's EMR linked to the requested medical concept, including those phrases in the natural language medical notes processed by natural language request processing engine 120, such that these medically relevant phrases may be returned to the medical professional as a response to their inquiry. Thus, natural language request processing engine 120 automatically finding medically relevant phrases utilizing a process that is not dependent on rules but, rather, is linked to anchor medical concepts. Thus, natural language request processing engine 120 automatically classifies medically relevant phrases over a wide and variable set of categories and combines phrases to capture the appropriate level of context. Thus, the present invention provides a mechanism for automatically finding and classifying clinically relevant phrases that is different and better than prior methods and provides a generalized approach that is not dependent on rules but rather is linked to anchor clinical concepts.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300, which may be a cognitive system such as cognitive system 100 described in FIG. 1, that is configured to extract the medically relevant portions of text within the patient's EMR for presentation to a medical professional. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, area of interest 318. The area of interest 318 may include, for example, elements, concepts, terms, parameters, or the like, in order to retrieve medically relevant content from the patient's EMRs 322 for patient 302. Any information about the patient 302 that may be relevant to a cognitive evaluation of the patient by the healthcare cognitive system 300 may be included in the request 308 and/or patient attributes 318.

Healthcare cognitive system 300 provides a cognitive system that is specifically configured to perform an implementation specific healthcare oriented cognitive operation. In the depicted example, this healthcare oriented cognitive operation is directed to providing medically relevant information 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and area of interest 318 utilizing information gathered from the medical corpus and other source data 326, treatment guidance data 324, and the patient EMRs 322 associated with the patient 302 to generate medically relevant information 328. Medically relevant information 328 may be presented with associated supporting evidence, obtained from the patient data sources 322-326, indicating the reasoning as to why medically relevant information 328 is being provided.

For example, based on request 308 and area of interest 318, the healthcare cognitive system 300 may operate on the request to parse request 308 and area of interest 318 to determine what is being requested and the criteria upon which the request is to be generated as identified by area of interest 318, and may perform various operations for generating queries that are sent to the data sources 322-326 to retrieve data, identify medically relevant information (or answers to the input question), and provides supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to include natural language request processing engine 340. Natural language request processing engine 340 comprises natural language processing engine 342, lexical concept extractor 344, model generator 346, and extraction engine 348. In the initial stage of processing, natural language request processing engine 340 receives request 308 from user 306 indicating area of interest 318 that user 306 would like to identify from the unstructured text of the patient's electronic medical records (EMR) 322, i.e. medical notes made by other medical professionals. For example, if user 306 is interested in seeing if patient 302 has a history of 'Hypertension,' user 306 will enter "hypertension" into natural language request processing engine 340. Accordingly, natural language processing engine 342 analyzes the structure of unstructured text in the patient's EMR 322 using known natural language processing techniques, including part-of-speech tagging, dependency parsing, negation detection, or the like. Lexical concept extractor 344 then identifies medical concepts in the unstructured text that matches the area of interest 318 entered by user 306 but also related medical concepts related to the area of interest 318 reflected in the medical corpus and other source data 326. That is, there are multiple ways in which medical professionals may mention hypertension when describing a patient. Thus, using related medical concepts, lexical concept extractor 344 may identify hypertension as well as surface variations such as 'HT' or 'HTN', as well as semantic variations such as 'High Blood Pressure' or 'Hypertensive disease NOS' or 'BP+' etc.

Once the structure and content of the unstructured text has been analyzed, model generator 346 constructs a Conditional Random Field (CRF) model as an undirected graphical model. In the undirected graphical model, model generator 346 constructs a representation such that each concept in the unstructured text is represented by a node. Model generator 346 then links these nodes together in a linear fashion such that a node is linked to both the concept found directly before the concept in the unstructured text and the concept found directly after the concept in the unstructured text.

Model generator 346 also constructs an additional link to a latent variable node, representing the label to be inferred. In order to infer the label, model generator 346 utilizes annotated data of sentences with medical phrases. Model generator 346 labels concepts in the ground truth text that begin a phrase of interest as a start of phrase label, while also labeling instances within the phrase with an internal phrase label. Model generator 346 also identified phrase endings by examining the label associated with the next concept in the sentence. Thus, if model generator 346 identifies a next concept as a phrase start label, then the previous internal phrases is relabeled as an end of the phrase.

To generalize the associations present in the annotated data, model generator 346 utilizes an array of discriminative features. These features are extracted from the concept information available within the linked ontology, the natural language processing analysis of the unstructured text, the words in the unstructured text found near the concept of interest, or the like. The linear connectedness of the graphical model ensures that each concept within the unstructured text is dependent on the concepts immediately preceding the concept and the concepts immediately following the concept, enabling model generator 346 to discover which concepts are appropriately grouped within the same phrase. In this manner, model generator 346 discovers text phrases with an underlying conceptual anchoring, enabling model generator 346 to capture the necessary context while still benefiting from the ontology information associated with each concept.

Having identified one or more medically relevant phrases in the unstructured text and associating them with medical concepts as anchor points, extraction engine 348 extracts each one or more medically relevant phrases and returns the one or more medically relevant phrases to user 306 who requested the information about a particular medical concept or related medical concept. Thus, if user 306 wants to know about a patient's particular condition, the related medical concepts may be determined and then used to identify the medically relevant phrases within the patient's EMR linked to the requested medical concept, including those phrases in the natural language medical notes processed by natural language request processing engine 340, such that these medically relevant phrases may be returned to user 306 as a response to their inquiry. Thus, natural language request processing engine 340 automatically finds medically relevant phrases utilizing a process that is not dependent on rules but, rather, is linked to anchor medical concepts.

Additionally, natural language request processing engine 340 also comprises categorization engine 350 that categorizing medically relevant phrases into medical categories or buckets, which have associated labels. Categorization engine 350 then utilizes these labels to analyze other phrases in the natural language content to determine whether these other phrases are associated with the requested medical concept. Determinations as to whether to merge phrases in the same natural language content, based on phrases being associated with a same category, may then be made. A CRF model approach may be used to determine whether to merge phrases.

For example, given an identified first medically relevant phrase from the unstructured text, categorization engine 350 categorizes the medically relevant phrase into a predefined category or bucket, which has label associated with the category of the medically relevant phrase. Categorization engine 350 utilizes the category or bucket labels as a basis for identifying other phrases in the unstructured text that are associated with similar concepts and that may be categorized into the same category. If another phrase is identified in the unstructured text that may be categorized in the same category based on a correlation of the labels of the category with the medically relevant phrase or anchor point associated with the medically relevant phrase, categorization engine 350 determines Whether the other medically relevant phrases should be merged with the identified and categorized first medically relevant phrase to generate a merged phrase associated with the category and clinical concept anchor point or the original medically relevant phrase. This determination of whether to merge phrases may be performed based on a set of conditional random fields (CRF), for example. Therefore, once phrases have been identified and categorized, and additional CRF model is constructed to perform the merging of phrases. While not directly anchored to medical concepts as performed by model generator 346 to produce larger phrases, the observed nodes of the CRF model utilized in merging are the phrases produced as output of the previous CFR models constructed by model generator 346. In this way the CRF model generated by categorization engine 350 inherits the properties of the underlying CRF model, including its concept anchors.

To identify the need for merging, categorization engine 350 constructs a CRF model anchored to these previously identified medically relevant phrases. The structure of this CRF model is linear, such that each phrase is represented as a node with a single edge connecting the node to the preceding medically relevant phrases and following medically relevant phrases in unstructured text. Each node also has an edge connecting it with a latent variable, representing the label of interest to be inferred. Much like the previous CRF model which categorization engine 350 works on top of, the labels of interest are represented by phrase start, phrase internal, and phrase end labels associated with each of the clinical categories.

Once the CRF model has been constructed, categorization engine 350 utilizes annotated data to establish a ground truth for model construction. To ensure the model is able to successfully learn how to combine phrases, categorization engine 350 constructs a discriminative feature space from features extracted from several source, such as features derived from the NLP-based analysis of unstructured text and document structure, concept ontology information, adjacent non-concept words, or the like. In addition to this, the output of the previous CRF model provides features for phrase labels. The label associated with the phrase as well as the classifiers probability distribution over all possible labels are included in the feature set. If the CFR model trained with the ground truth and discriminative feature space indicates that one or more select medically relevant phrases should be merged, categorization engine 350 merges the select medically relevant phrases.

Having identified and merged concepts that are categorized into a category that is relevant to the area of interest identified by user 306, extraction engine 348 extracts each one or more medically relevant phrases and returns the one or more medically relevant phrases to user 306 who requested the information about a particular medical concept or related medical concept. Thus, if user 306 wants to know about a patient's particular condition, the related medical concepts may be determined and then used to identify the medically relevant phrases within the patient's EMR linked to the requested medical concept, including those phrases in the natural language medical notes processed by natural language request processing engine 340, such that these medically relevant phrases may be returned to user 306 as a response to their inquiry as medically relevant information 328. Thus, natural language request processing engine 340 automatically finding medically relevant phrases utilizing a process that is not dependent on rules but, rather, is linked to anchor medical concepts. Thus, natural language request processing engine 340 automatically classifies medically relevant phrases over a wide and variable set of categories and combines phrases to capture the appropriate level of context. Thus, the present invention provides a mechanism for automatically finding and classifying clinically relevant phrases that is different and better than prior methods and provides a generalized approach that is not dependent on rules but rather is linked to anchor clinical concepts.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 7:
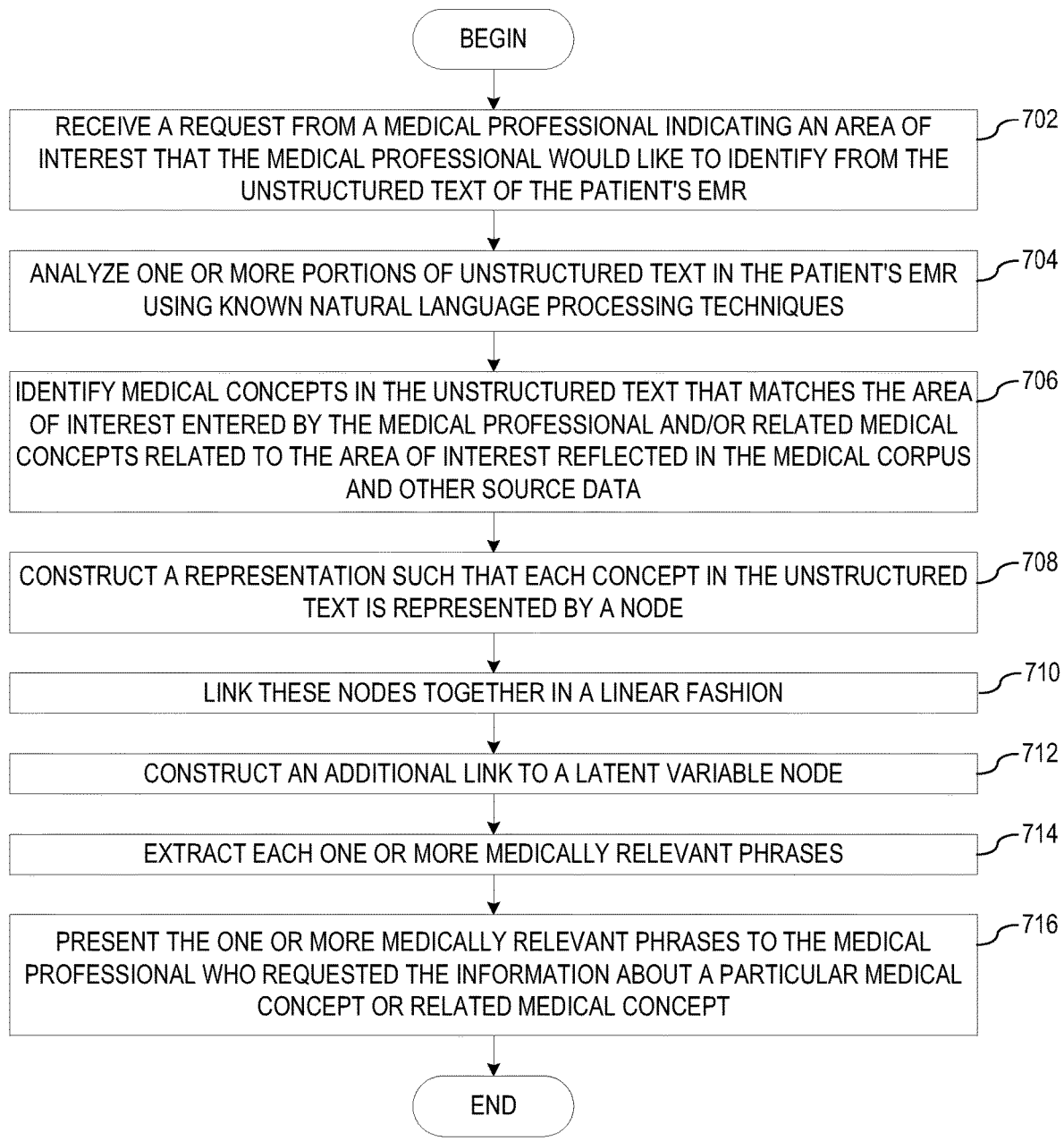
FIG. 7 depicts a functional block diagram of operations performed by a natural language request processing engine in automatically extracting medically relevant portions of text within the patient's EMR for presentation to a medical professional in accordance with an illustrative embodiment.

FIG. 7 depicts a functional block diagram of operations performed by a natural language request processing engine in automatically extracting medically relevant portions of text within the patient's EMR for presentation to a medical professional in accordance with an illustrative embodiment. As the operation begins, the natural language request processing engine receives a request from the medical professional indicating an area of interest that the medical professional would like to identify from the unstructured text of the patient's electronic medical records (EMR) (step 702). Utilizing the area of interest, the natural language request processing engine analyzes one or more portions of unstructured text in the patient's EMR using known natural language processing techniques, including part-of-speech tagging, dependency parsing, negation detection, or the like (step 704). The natural language request processing engine then identifies medical concepts in the unstructured text that matches the area of interest entered by the medical professional and/or related medical concepts related to the area of interest reflected in the medical corpus and other source data (step 706). That is, there are multiple ways in which medical professionals may mention hypertension when describing a patient. Thus, using related medical concepts, the natural language request processing engine may identity hypertension as well as surface variations such as 'HT' or 'HTN', as well as semantic variations such as 'High Blood Pressure' or 'Hypertensive disease NOS' or 'BP+' etc.

Once the structure and content of the unstructured text has been analyzed, the natural language request processing engine constructs a Conditional Random Field (CRF) model as an undirected graphical model. In the undirected graphical model, the natural language request processing engine constructs a representation such that each concept in the unstructured text is represented by a node (step 708), The natural language request processing engine then links these nodes together in a linear fashion such that a node is linked to both the concept found directly before the concept in the unstructured text and the concept found directly after the concept in the unstructured text (step 710).

The natural language request processing engine also constructs an additional link to a latent variable node, representing the label to be inferred (step 712). In order to infer the label, the natural language request processing engine utilizes annotated data of sentences with medical phrases. The natural language request processing engine labels concepts in the ground truth text that begin a phrase of interest as a start of phrase label, while also labeling instances within the phrase with an internal phrase label. The natural language request processing engine also identified phrase endings by examining the label associated with the next concept in the sentence. Thus, if the natural language request processing engine identifies a next concept as a phrase start label, then the previous internal phrases is relabeled as an end of the phrase.

To generalize the associations present in the annotated data, the natural language request processing engine utilizes an array of discriminative features. These features are extracted from the concept information available within the linked ontology, the natural language processing analysis of the unstructured text, the words in the unstructured text found near the concept of interest, or the like. The linear connectedness of the graphical model ensures that each concept within the unstructured text is dependent on the concepts immediately preceding the concept and the concepts immediately following the concept, enabling the natural language request processing engine to discover which concepts are appropriately grouped within the same phrase. In this manner, the natural language request processing engine discovers text phrases with an underlying conceptual anchoring, enabling the natural language request processing engine to capture the necessary context while still benefiting from the ontology information associated with each concept.

Having identified one or more medically relevant phrases in the unstructured text and associating them with medical concepts as anchor points, the natural language request processing engine extracts each one or more medically relevant phrases (step 714). The natural language request processing engine then presents the one or more medically relevant phrases to the medical professional who requested the information about a particular medical concept or related medical concept (step 716), with the operation terminating thereafter.

Thus, if a medical professional wants to know about a patient's particular condition, the related medical concepts may be determined and then used to identify the medically relevant phrases within the patient's EMR linked to the requested medical concept, including those phrases in the natural language medical notes processed by the natural language request processing engine, such that these medically relevant phrases may be returned to the medical professional as a response to their inquiry. Thus, the natural language request processing engine automatically finds medically relevant phrases utilizing a process that is not dependent on rules but, rather, is linked to anchor medical concepts.

Figure 8:
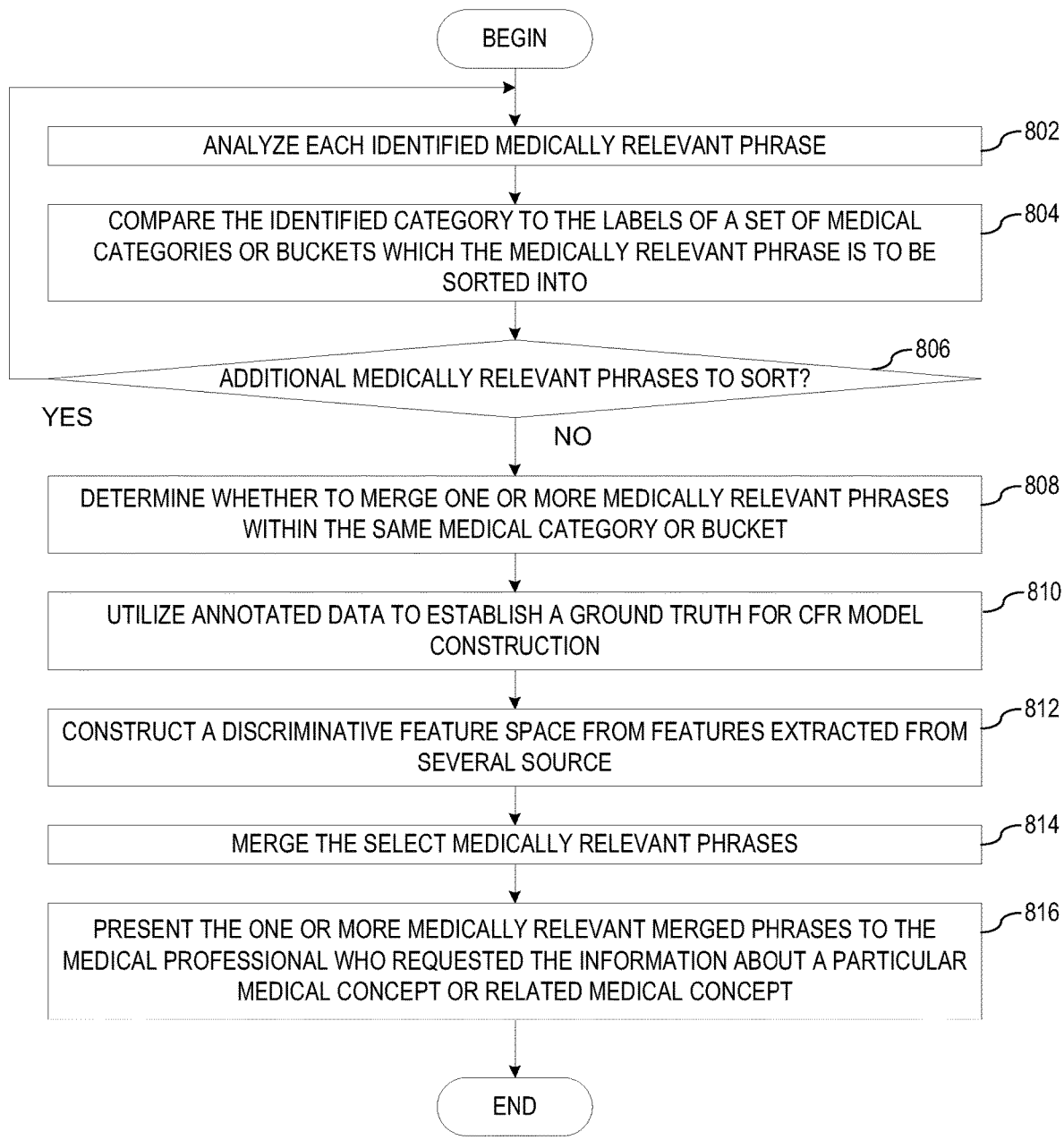
FIG. 8 depicts a functional block diagram of operations performed by a natural language request processing engine in categorizing and merging medically relevant portions of text within the patient's EMR for presentation to a medical professional in accordance with an illustrative embodiment.

FIG. 8 depicts a functional block diagram of operations performed by a natural language request processing engine in categorizing and merging medically relevant portions of text within the patient's EMR for presentation to a medical professional in accordance with an illustrative embodiment. As the operation begins, the natural language request processing engine analyzes each medically relevant phrase identified from the process described in FIG. 7 to identify a category of the medically relevant phrase (step 802). The natural language request processing engine compares the identified category to the labels of a set of medical categories or buckets which the medically relevant phrase is to be sorted into (step 804). Upon identifying a medical category or bucket to sort the medically relevant phrase into, the natural language request processing engine determines whether there are additional medically relevant phrases to sort (step 806). If at step 806 there are other medically relevant phrases to sort, the operation returns to step 802.

If at step 806 there are no other medically relevant phrases to sort, for each medical category or bucket, the natural language request processing engine determines whether to merge one or more medically relevant phrases within the same medical category or bucket (step 808). To do this, the natural language request processing engine constructs an additional CRF model that is linear, such that each phrase is represented as a node with a single edge connecting the node to the preceding medically relevant phrases and following medically relevant phrases in unstructured text. Each node also has an edge connecting it with a latent variable, representing the label of interest to be inferred. Much like the previous CRF model, the labels of interest are represented by phrase start, phrase internal, and phrase end labels associated with each of the clinical categories.

Once the CRF model has been constructed, the natural language request processing engine utilizes annotated data to establish a ground truth for CFR model construction (step 810). To ensure the model is able to successfully learn how to combine phrases, the natural language request processing engine constructs a discriminative feature space from features extracted from several source (step 812), such as features derived from the NLP-based analysis of unstructured text and document structure, concept ontology information, adjacent non-concept words, or the like. If the CFR model and discriminative feature space indicates that one or more select medically relevant phrases should be merged, the natural language request processing engine merges the select medically relevant phrases (step 814). The natural language request processing engine then presents the one or more medically relevant merged phrases to the medical professional who requested the information about a particular medical concept or related medical concept (step 816), with the operation terminating thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for phrase-based extraction that is anchored to concepts, allowing for the medically relevant portions of text within the patient's EMR to be extracted. Utilizing Natural Language Processing (NLP), unstructured (natural language) text within the patient's EMR is analyzed and, based on the results of the NLP, concepts are extracted and those concepts are linked to an ontology. The concepts provide anchor points for phrases in the unstructured text. The text corresponding to a similar concept is then concatenated to generate the phrases that are anchored to the concepts and thereby generate medically relevant phrases that are then provided to the medical professional requesting information regarding the corresponding concept (anchor point).

Additionally, the illustrative embodiments provide mechanisms for categorizing the medically relevant phrases into medical categories. Labels are associated with the medical categories and these labels are used to analyze other medically relevant phrases in the natural language content of the patient's EMR to determine whether which medical category these other medically relevant phrases are associated with. Determinations are then made with regard to merging medically relevant phrases in the same natural language content, based on medically relevant phrases being associated with a same medical category. A Conditional Random Field approach may be used to determine whether to merge medically relevant phrases. That is, Conditional Random Field (CRF) models may be used to model what is a medically relevant phrase. The CRF models model the sequential aspect of a medically relevant phrase and thus, may be used to perform pattern recognition with a portion of unstructured text. Thus, the mechanisms describe medically relevant phrases as CRF models and find these CRT models in segmented text generated by the NLP of the patient's EMR where the segments are specified by the anchor points associated with the concepts.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable fir storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the forum disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions which are executed by the processor to cause the processor to be configured to implement a natural language request processing engine, the method comprising:

responsive to receiving a request for information specifying a concept of interest, performing, by the natural language request processing engine, natural language processing on a plurality of phrases in a portion of unstructured text in an electronic data structure to generate textual characteristics of the portion of unstructured text;

linking, by the natural language request processing engine, each phrase in the portion of unstructured text to the concept of interest and one or more concepts specified in at least one ontological data structure, based on the textual characteristics of the portion of unstructured text;

generating, by the natural language request processing engine, an undirected graphical model of the portion of unstructured text such that each particular concept in the unstructured text is represented by a node and such that each particular concept is linked to another concept in the unstructured text based on each particular concept and respective another concept linked to the same phrase; and processing, by the natural language request processing engine, the request for information specifying the concept of interest based on the undirected graphical model of the portion of unstructured text, wherein the processing of the request for information comprises retrieving the same phrase as a response to the request in response to determining that the same phrase has a linked concept in the one or more concepts that matches the concept of interest specified in the request.

2. The method of claim 1, wherein, in the model of the portion of unstructured text, each concept in the one or more concepts is linked in the model such that a particular concept is linked to either a concept appearing prior to the particular concept in the portion of unstructured text or a concept appearing after the particular concept in the portion of unstructured text.

3. The method of claim 1, wherein generating the model of the portion of unstructured text comprises:
constructing, by the natural language request processing engine, a representation such that each concept in the unstructured text is represented by a node.

4. The method of claim 3, wherein each node in the model of the portion of unstructured text has an associated latent variable node link representing a label to be inferred for the node in the model.

5. The method of claim 4, wherein each of the associated latent variable node links associated with nodes in the model of the portion of unstructured text has an associated label selected from a set comprising a start label indicating a start of a relevant phrase, an internal label indicating an internal relevant phrase, and an end label indicating an end relevant phrase.

6. The method of claim 1, further comprising:
performing, by the natural language request processing engine, a machine learning operation to discover unstructured textual phrases with an underlying conceptual anchor based on the generated model, wherein each of the discovered unstructured textual phrases include the context of the unstructured textual phrase and the associated ontology information associated with the underlying conceptual anchor.

7. The method of claim 1, wherein processing the request for information specifying the concept of interest based on the model of the portion of unstructured text further comprises:
extracting, by the natural language request processing engine, one or more medically relevant phrases from the portion of unstructured text, wherein the at least one phrase presented as the response to the request is retrieved from the extracted one or more medically relevant phrases.

8. A computer program product comprising a computer readable storage medium having a computer readable program stored therein, wherein the computer readable program, when executed on a computing device, causes the computing device to implement a natural language request processing engine which operates to:
responsive to receiving a request for information specifying a concept of interest, perform natural language processing on a plurality of phrases in a portion of unstructured text in an electronic data structure to generate textual characteristics of the portion of unstructured text;

link each phrase in the portion of unstructured text to the concept of interest and one or more concepts specified in at least one ontological data structure, based on the textual characteristics of the portion of unstructured text;

generate an undirected graphical model of the portion of unstructured text such that each particular concept in the unstructured text is represented by a node and such that each particular concept is linked to another concept in the unstructured text based on each particular concept and respective another concept linked to the same phrase; and process the request for information specifying the concept of interest based on the undirected graphical model of the portion of unstructured text, wherein the processing of the request for information comprises retrieving the same phrase as a response to the request in response to determining that the same phrase has a linked concept in the one or more concepts that matches the concept of interest specified in the request.

9. The computer program product of claim 8, wherein, in the model of the portion of unstructured text, each concept in the one or more concepts is linked in the model such that a particular concept is linked to either a concept appearing prior to the particular concept in the portion of unstructured text or a concept appearing after the particular concept in the portion of unstructured text.

10. The computer program product of claim 8, wherein the computer readable program to generate the model of the portion of unstructured text further causes the computing device to implement the natural language request processing engine which operates to:
construct a representation such that each concept in the unstructured text is represented by a node.

11. The computer program product of claim 10, wherein each node in the model of the portion of unstructured text has an associated latent variable node link representing a label to be inferred for the node in the model.

12. The computer program product of claim 11, wherein each of the associated latent variable node links associated with nodes in the model of the portion of unstructured text has an associated label selected from a set comprising a start label indicating a start of a relevant phrase, an internal label indicating an internal relevant phrase, and an end label indicating an end relevant phrase.

13. The computer program product of claim 8, the computer readable program further causes the computing device to implement the natural language request processing engine which operates to:
perform a machine learning operation to discover unstructured textual phrases with an underlying conceptual anchor based on the generated model, wherein each of the discovered unstructured textual phrases include the context of the unstructured textual phrase and the associated ontology information associated with the underlying conceptual anchor.

14. The computer program product of claim 8, wherein the computer readable program to process the request for information specifying the concept of interest based on the model of the portion of unstructured text further causes the computing device to implement the natural language request processing engine which operates to:
extract one or more medically relevant phrases from the portion of unstructured text, wherein the at least one phrase presented as the response to the request is retrieved from the extracted one or more medically relevant phrases.

15. An apparatus comprising:
a processor; and
a memory coupled to the processor, wherein the memory comprises instructions which, when executed by the processor, cause the processor to implement a natural language request processing engine which operates to:
responsive to receiving a request for information specifying a concept of interest, perform natural language processing on a plurality of phrases in a portion of unstructured text in an electronic data structure to generate textual characteristics of the portion of unstructured text;
link each phrase in the portion of unstructured text to the concept of interest and one or more concepts specified in at least one ontological data structure, based on the textual characteristics of the portion of unstructured text;
generate an undirected graphical model of the portion of unstructured text such that each particular concept in the unstructured text is represented by a node and such that each particular concept is linked to another concept in the unstructured text based on each particular concept and respective another concept linked to the same phrase; and
process the request for information specifying the concept of interest based on the undirected graphical model of the portion of unstructured text, wherein the processing of the request for information comprises retrieving the same phrase as a response to the request in response to determining that the same phrase has a linked concept in the one or more concepts that matches the concept of interest specified in the request.

16. The apparatus of claim 15, wherein, in the model of the portion of unstructured text, each concept in the one or more concepts is linked in the model such that a particular concept is linked to either a concept appearing prior to the particular concept in the portion of unstructured text or a concept appearing after the particular concept in the portion of unstructured text.

17. The apparatus of claim 15, wherein the instructions to generate the model of the portion of unstructured text further cause the processor to implement the natural language request processing engine which operates to:
construct a representation such that each concept in the unstructured text is represented by a node.

18. The apparatus of claim 17, wherein each node in the model of the portion of unstructured text has an associated latent variable node link representing a label to be inferred for the node in the model.

19. The apparatus of claim 18, wherein each of the associated latent variable node links associated with nodes in the model of the portion of unstructured text has an associated label selected from a set comprising a start label indicating a start of a relevant phrase, an internal label indicating an internal relevant phrase, and an end label indicating an end relevant phrase.

20. The apparatus of claim 15, the instructions further cause the processor to implement the natural language request processing engine which operates to:
perform a machine learning operation to discover unstructured textual phrases with an underlying conceptual anchor based on the generated model, wherein each of the discovered unstructured textual phrases include the context of the unstructured textual phrase and the associated ontology information associated with the underlying conceptual anchor.

* * * * *